United States Patent
Tanaka et al.

(10) Patent No.: US 11,479,780 B2
(45) Date of Patent: Oct. 25, 2022

(54) FUSION PROTEIN FOR CONTROLLING EPIGENOMIC STATE, AND USE THEREOF

(71) Applicant: KABUSHIKI KAISHA TOYOTA CHUO KENKYUSHO, Nagakute (JP)

(72) Inventors: Hidenori Tanaka, Nagakute (JP); Akinori Ikeuchi, Nagakute (JP); Risa Onoda, Nagakute (JP); Hiroki Sugimoto, Nagakute (JP); Nobuhiko Muramoto, Nagakute (JP)

(73) Assignee: KABUSHIKI KAISHA TOYOTA CHUO KENKYUSHO, Nagakute (JP)

( * ) Notice: Subject to any disclaimer, the term of this patent is extended or adjusted under 35 U.S.C. 154(b) by 182 days.

(21) Appl. No.: 16/797,076

(22) Filed: Feb. 21, 2020

(65) Prior Publication Data

US 2020/0270620 A1 Aug. 27, 2020

(30) Foreign Application Priority Data

Feb. 21, 2019 (JP) .............................. JP2019-029415

(51) Int. Cl.
  *C12N 15/81* (2006.01)
  *C12N 15/62* (2006.01)
  *C12N 9/10* (2006.01)

(52) U.S. Cl.
  CPC ........... *C12N 15/81* (2013.01); *C12N 9/1003* (2013.01); *C12N 9/1025* (2013.01); *C12N 15/62* (2013.01); *C07K 2319/00* (2013.01)

(58) Field of Classification Search
  None
  See application file for complete search history.

(56) References Cited

U.S. PATENT DOCUMENTS

| | | | |
|---|---|---|---|
| 9,388,430 B2 | 7/2016 | Liu et al. | |
| 2008/0166809 A1 | 7/2008 | Ohta et al. | |
| 2011/0035846 A1 | 2/2011 | Takagi et al. | |
| 2011/0277189 A1 | 11/2011 | Kondo et al. | |
| 2020/0063114 A1* | 2/2020 | Fauser | C12N 15/102 |

FOREIGN PATENT DOCUMENTS

| | | |
|---|---|---|
| JP | 4158920 B2 | 10/2008 |
| JP | 2009-213426 A | 9/2009 |
| JP | 2009-532053 A | 9/2009 |
| JP | 2011-160798 A | 8/2011 |
| JP | 2012-044883 A | 3/2012 |
| JP | 2015-509957 A | 4/2015 |
| WO | 2007/128982 A2 | 11/2007 |
| WO | 2013/130807 A1 | 9/2013 |
| WO | 2015/020218 A1 | 2/2015 |

OTHER PUBLICATIONS

Grimmer et al., "Analysis of an artificial zinc finger epigenetic modulator: widespread binding but limited regulation", Nucleic Acids Research, 2014, vol. 42, No. 16, pp. 10856-10868. doi: 10.1093/nar/gku708.*
Thakore, et al., "Editing the Epigenome: Technologies for Programmable Transcriptional Modulation and Epigenetic Regulation," Nature Methods, 2016, pp. 127-137, 13(2).
Nihongaki, et al., "CRISPR-Cas9-based photoactivatable transcription systems to induce neuronal differentiation," Nature Methods, 2017, pp. 963-966 and 4 pages of supporting material, 14(10).
Cao, W. and Barany, F. "Identification of TaqI Endonuclease Active Site Residues by Fe2+-mediated Oxidative Cleavage," J. Biol. Chem., 1998, pp. 33002-33010, vol. 273, No. 49.
Kim, S. A., "Localization of Iron in *Arabidopsis* Seed Requires the Vacuolar Membrane Transporter VIT1," Science, 2006, pp. 1295-1298, 314(5803).
Keung, A. J. et al., "Using Targeted Chromatin Regulators to Engineer Combinatorial and Spatial Transcriptional Regulation," Cell, 2014, pp. 110-120, 158(1).
Sakuma, Y. et al., "Dual function of an *Arabidopsis* transcription factor DREB2A in water-stress-responsive and heat-stress-responsive gene expression," Proceedings of the National Academy of Sciences, 2006, pp. 18822-18827, 103(49).
Jun. 8, 2021 Office Action issued in Japanese Patent Application No. 2019-029415.

* cited by examiner

*Primary Examiner* — Suzanne M Noakes
(74) *Attorney, Agent, or Firm* — Oliff PLC

(57) ABSTRACT

Epigenomic states of genome DNA are altered at multiple sites to rapidly change traits by providing a fusion protein including a first region that defines a polypeptide capable of binding sequence-specifically to multiple sites on genome DNA and a second region that defines a polypeptide capable of regulating an epigenomic state.

22 Claims, 8 Drawing Sheets
Specification includes a Sequence Listing.

SEQUENCE LISTING

```
<160> NUMBER OF SEQ ID NOS: 18

<210> SEQ ID NO 1
<211> LENGTH: 33
<212> TYPE: DNA
<213> ORGANISM: Artificial
<220> FEATURE:
<223> OTHER INFORMATION: Primer

<400> SEQUENCE: 1
gccacctggg agttggccgc caggggata gat                            33
```

```
<210> SEQ ID NO 2
<211> LENGTH: 33
<212> TYPE: DNA
<213> ORGANISM: Artificial
<220> FEATURE:
<223> OTHER INFORMATION: Primer

<400> SEQUENCE: 2
atctatcccc tgggcggcca actcccaggt ggc                              33

<210> SEQ ID NO 3
<211> LENGTH: 24
<212> TYPE: DNA
<213> ORGANISM: Artificial
<220> FEATURE:
<223> OTHER INFORMATION: Primer

<400> SEQUENCE: 3
cgccagggtt ttcccagtca cgac                                        24

<210> SEQ ID NO 4
<211> LENGTH: 22
<212> TYPE: DNA
<213> ORGANISM: Artificial
<220> FEATURE:
<223> OTHER INFORMATION: Primer

<400> SEQUENCE: 4
tcacacagga aacagctatg ac                                          22

<210> SEQ ID NO 5
<211> LENGTH: 20
<212> TYPE: DNA
<213> ORGANISM: Artificial
<220> FEATURE:
<223> OTHER INFORMATION: Primer

<400> SEQUENCE: 5
cggctaccac atccaaggaa                                             20

<210> SEQ ID NO 6
<211> LENGTH: 21
<212> TYPE: DNA
<213> ORGANISM: Artificial
<220> FEATURE:
<223> OTHER INFORMATION: Primer

<400> SEQUENCE: 6
tgtcactacc tccccgtgtc a                                           21

<210> SEQ ID NO 7
<211> LENGTH: 21
<212> TYPE: DNA
<213> ORGANISM: Artificial
<220> FEATURE:
<223> OTHER INFORMATION: Primer

<400> SEQUENCE: 7
ccatgtattt tgcaatgcgt g                                           21

<210> SEQ ID NO 8
<211> LENGTH: 21
<212> TYPE: DNA
<213> ORGANISM: Artificial
<220> FEATURE:
<223> OTHER INFORMATION: Primer
```

<400> SEQUENCE: 8
tgtggagcac ctcgaatctc t                                              21

<210> SEQ ID NO 9
<211> LENGTH: 390
<212> TYPE: DNA
<213> ORGANISM: Artificial
<220> FEATURE:
<223> OTHER INFORMATION: Artificial promoter

<400> SEQUENCE: 9
cgacatcgtc gaatatgatt actcaccaat cgatttaccg gttcctttgt cgatatcatg     60
ttgggacgct cgaaggcttt atttagttgt cgactgatac ttgacttcat cgagactttc    120
agaccacgat cgatggtcac taatcctcga gcagatccgc caggcgtgta tatatagcgt    180
ggatggccag gcaactttag tgctgacaca tacaggcata tatatatgtg tgcgacgaca    240
catgatcata tggcatgcat gtgctctgta tgtatataaa actcttgttt tcttcttttc    300
tctaaatatt ctttccttat acattaggac ctttgcagca taaattacta tacttctata    360
gacacacaaa cacaaataca cacactaaat                                     390

<210> SEQ ID NO 10
<211> LENGTH: 270
<212> TYPE: DNA
<213> ORGANISM: Artificial
<220> FEATURE:
<223> OTHER INFORMATION: Artificial promoter

<400> SEQUENCE: 10 acaggccect tttcctttga cgatatcatg taattagtta tgtcacgctt acattcacgc     60
cctcctccca catccgctct aaccgaaaag gaaggagtta gacaacctga agtctaggtc    120
cctatttatt tttttaata gttatgttag tattaagaac gttatttata tttcaaatttt    180
ttcttttttt tctgtacaaa cgcgtgtacg catgtaacat tatactgaaa accttgcttg    240
agaaggtttt gggacgcacg aaggctttaa                                     270

<210> SEQ ID NO 11
<211> LENGTH: 240
<212> TYPE: DNA
<213> ORGANISM: Artificial
<220> FEATURE:
<223> OTHER INFORMATION: Artificial promoter

<400> SEQUENCE: 11
gcagatccgc caggcgtgta tatatagcgt ggatggccag gcaactttag tgctgacaca     60
tacaggcata tatatatgtg tgcgacgaca catgatcata tggcatgcat gtgctctgta    120
tgtatataaa actcttgttt tcttcttttc tctaaatatt ctttccttat acattaggac    180
ctttgcagca taaattacta tacttctata gacacacaaa cacaaataca cacactaaat    240

<210> SEQ ID NO 12
<211> LENGTH: 22
<212> TYPE: DNA
<213> ORGANISM: Artificial
<220> FEATURE:
<223> OTHER INFORMATION: Primer

<400> SEQUENCE: 12
tttcatcctg gtagactgga ca                                             22

```
<210> SEQ ID NO 13
<211> LENGTH: 24
<212> TYPE: DNA
<213> ORGANISM: Artificial
<220> FEATURE:
<223> OTHER INFORMATION: Primer

<400> SEQUENCE: 13
cacatctctt agatgatcca cacc                                              24

<210> SEQ ID NO 14
<211> LENGTH: 20
<212> TYPE: DNA
<213> ORGANISM: Artificial
<220> FEATURE:
<223> OTHER INFORMATION: Primer

<400> SEQUENCE: 14
gattttcaaa tttcgtcccc                                                   20

<210> SEQ ID NO 15
<211> LENGTH: 22
<212> TYPE: DNA
<213> ORGANISM: Artificial
<220> FEATURE:
<223> OTHER INFORMATION: Primer

<400> SEQUENCE: 15
ctccactctg atcataaact gc                                                22

<210> SEQ ID NO 16
<211> LENGTH: 21
<212> TYPE: DNA
<213> ORGANISM: Artificial
<220> FEATURE:
<223> OTHER INFORMATION: Primer

<400> SEQUENCE: 16
acccttcacg agtttacatg c                                                 21

<210> SEQ ID NO 17
<211> LENGTH: 18
<212> TYPE: DNA
<213> ORGANISM: Artificial
<220> FEATURE:
<223> OTHER INFORMATION: Primer

<400> SEQUENCE: 17
gcgttagggt gctcgatg                                                     18

<210> SEQ ID NO 18
<211> LENGTH: 8
<212> TYPE: PRT
<213> ORGANISM: Artificial Sequence
<220> FEATURE:
<223> OTHER INFORMATION: nuclear translocation signal

<400> SEQUENCE: 18

Pro Pro Lys Lys Lys Arg Lys Val
1               5
```

###FUSION PROTEIN FOR CONTROLLING EPIGENOMIC STATE, AND USE THEREOF

The present application contains a Sequence Listing that has been submitted electronically in ASCII format and is hereby incorporated by reference in its entirety. The ASCII copy, created on Jun. 16, 2022, is named Substitute_Sequence_Listing_ST25.txt and is 4,411 bytes in size.

TECHNICAL FIELD

The present application relates to a fusion protein for regulating an epigenomic state, and to a use thereof.

CROSS REFERENCE TO RELATED APPLICATIONS

This application is related to Japanese Patent Application No. 2019-029415 filed on Feb. 21, 2019 and claims priority to the Japanese application entire contents of which are incorporated by reference herein.

BACKGROUND ART

Increasing plant biomass production can have the effect of not only increasing food production, but also protecting the global environment, preventing global warming, and reducing emissions of greenhouse gasses. Consequently, techniques for increasing plant biomass production are of great industrial importance. Moreover, microorganisms are used effectively in various industries. For example, in bioethanol manufacture using polysaccharides such as cellulose as raw materials, yeasts having properties such as high heat resistance, high alcohol concentration resistance, and high alcohol synthesis ability are desirable for performing low-cost ethanol fermentation.

These properties associated with improved productivity and stress resistance in plants and yeasts are quantitative traits that are affected by expression of multiple genes rather than a single gene. Conventionally, modification of such traits that are affected by multiple genes has been achieved by repeated mutagenesis over several generations. This is because according to ordinary mutation treatments such as base substitutions and DNA deletions, the phenotypic changes induced by a single mutation treatment are normally small, and it is difficult to simultaneously affect multiple traits. It is known that in the case of such mutagenesis over multiple generations, multiple unnecessary mutations accumulate at the same time as useful mutations, and often necessary traits are also lost in the process. For these reasons, there is a need for development of systems capable of directly controlling a broad range of gene expression in order to modify traits that are controlled by multiple genes.

A chimera repressor has already been developed including a transcription inhibition domain linked to a transcription factor protein that plays a central role in controlling gene expression (CRES-T method, Patent Literature 1, Non Patent Literature 1). and this is reportedly able to induce phenotypes similar to knockouts.

As a method for specifically controlling individual gene expression, a method is already known for editing a genome through DNA breaks using TALEN or CRISPR/dCas9/gRNA as a DNA sequence recognition molecule (Patent Literature 2, 3). A method has also been reported for controlling epigenomic states by linking such a DNA sequence recognition molecule to a transcription control factor or epigenomic state control factor to thereby modify a specific DNA sequence (Non Patent Literature 2, 3). Like genome editing techniques, these techniques are aimed at regulating expression of specific genes.

Meanwhile, methods for obtaining various mutants by artificially inducing genetic recombination on genome DNA in actual plants and fungal cells have been reported as methods capable of efficiently performing large-scale genome reorganization (Patent Literature 4 to 6). With these methods, mutants can be efficiently obtained through genome DNA reorganization by artificially inducing so-called genome shuffling with restriction enzymes in plant cells and fungal cells.

CITATION LIST

Patent Literature

Patent Literature 1 Japanese Patent Application Publication No. 2009-213426
Patent Literature 2 WO 2015/020218
Patent Literature 3 U.S. Patent Specification No. 9388430
Patent Literature 4 Japanese Patent Application Publication No. 2012-44883
Patent Literature 5 Japanese Patent Application Publication No. 2011-160798
Patent Literature 6 Japanese Patent No. 4158920

Non Patent Literature

Non Patent Literature 1 Chemistry and Biology (Kagaku to Seibutsu), Vol. 52 (2014), No. 7, pp. 438-446
Non Patent Literature 2 Nature Methods, 2016, 13(2), 127
Non Patent Literature 3 Nature Methods. 2017, 14(10), 963

SUMMARY

However, much is still unknown regarding the principles of gene expression regulation using chimera repressors including transcription inhibition domains linked to transcription factor proteins. The greatest shortcoming is the fact that it is difficult to quantitatively evaluate effectiveness as long as the target gene of the transcription factor is unknown. In general, there are known to be few transcription factors for which the target genes are known (Non Patent Literature 3).

Moreover, because gene expression regulation using TALEN and CRISPR/dCas9/gRNA is always aimed at regulating expression of specific genes, it is thought to be unsuited to multiple gene expression control across a broad range of the genome. Other problems with this method include the difficulty of using it when the target gene has not been confirmed, as well as the longstanding off-target problem.

Furthermore, because artificial genome shuffling introduces a variety of mutations by DNA breaking and recombination across a broad range of the genome, there has been a risk that a variety of mutation information not related to gene expression control could accumulate within the living organism. Furthermore, genome breaking and recombination poses the risk of serious damage to cells.

Thus, at present no method has been discovered that is suited to directly controlling expression of multiple kinds of broad-ranging genes. This Description provides a suitable technology for such gene expression control.

The inventors thought that controlling epigenomic states would be an effective way of controlling gene expression across a broad range of the genome without modifying genetic information, and without breaking double-stranded DNA. We also thought that when aiming to control epigenomic states, it was important to provide a scaffold for linking multiple sites on the genome with a constant degree of sequence specificity. Moreover, we thought that controlling epigenomic states with this protein as a scaffold would be useful for controlling expression of a target gene when the target gene has not been identified, for efficiently modifying quantitative traits, for conferring new traits and the like, and for modification and functional analysis of epigenomic states.

Based on these ideas, the inventors focused on restriction enzymes. The inventors thought that if there were a polypeptide having only DNA binding property and lacking DNA breaking ability, it could be expected to function as a scaffold protein capable of binding sequence-specifically across a broad range of the genome. We then discovered as a result of various researches that a polypeptide obtaining by removing DNA break ability from a frequent restriction enzyme while leaving only the binding property could act as a sequence-specific scaffold protein on genome DNA. The inventors also discovered that epigenomic states could be controlled across a broad range of the genome without breaking DNA by linking a polypeptide that induces epigenomic state changes to this protein, and expressing the resulting fusion protein in cells. The present Description provides the following means.

[1] A fusion protein including a first region that defines a polypeptide capable of binding sequence-specifically to multiple sites on genome DNA and a second region that defines a polypeptide capable of regulating an epigenomic state.

[2] The fusion protein according to [1], wherein the polypeptide defined by the first region derives from a restriction enzyme and lacks DNA double-strand cleavage activity.

[3] The fusion protein according to [2], wherein the restriction enzyme is a frequent restriction enzyme.

[4] The fusion protein according to any one of [1] to [3], wherein the polypeptide defined by the first region derives from a 4-base recognition restriction enzyme and lacks DNA double-strand cleavage activity.

[5] The fusion protein according to any one of [1] to [4], wherein the polypeptide defined by the first region has an activity of recognizing and binding to a palindromic sequence in genome DNA.

[6] A fusion protein including a first region that defines a polypeptide derived from a frequent restriction enzyme, having an activity of recognizing and binding to a palindromic sequence in genome DNA, and lacking DNA double-strand cleavage activity, and a second region that defines a polypeptide capable of regulating an epigenomic state.

[7] The fusion protein according to any one of [1] to [6], wherein the polypeptide defined by the second region has DNA methylation activity, DNA demethylation activity and/or histone chemical modification activity.

[8] The fusion protein according to [7], wherein the histone chemical modification activity is selected from the group consisting of histone acetylation, histone deacetylation, histone methylation, histone demethylation, histone ubiquitination and histone deubiquitination.

[9] A method including the steps of:
preparing a fusion protein including a first region that defines a polypeptide capable of binding sequence-specifically to multiple sites on genome DNA and a second region that defines a polypeptide capable of regulating an epigenomic state, so that the fusion protein is capable of acting on the genome DNA, and
delivering the fusion protein to the sequence-specifically recognized sites on the genome DNA by taking advantage of the sequence-specific binding property of the first region, and allowing the second region to act on the genome DNA to alter an epigenomic state.

[10] The method according to [9], wherein the epigenomic states at the multiple sites on the genomic DNA are altered simultaneously.

[11] The method according to [9] or [10], wherein the fusion protein is allowed to act inductively.

[12] The method according to any one of [9] to [11], wherein a trait of an organism is altered.

[13] The method according to any one of [9] to [12], wherein a quantitative trait of an organism is altered.

[14] The method according to any one of [9] to [13], wherein the organism is a plant.

[15] The method according to any one of [9] to [13], wherein the organism is a yeast.

[16] The method according to any one of [9] to [13], wherein the genome DNA is genome DNA within an animal cell derived from a human.

[17] The method according to any one of [9] to [15], which is a method of breeding a non-human organism.

[18] A polynucleotide encoding the fusion protein according to any one of [1] to [8].

[19] A vector containing the polynucleotide according to [18].

[20] A cell containing the polynucleotide according to [18] or the vector according to [19].

[21] A kit including the fusion protein according to any one of [1] to [8], the polynucleotide according to [18], the vector according to [19] or the cell according to [20].

DESCRIPTION OF EMBODIMENTS

Figure 1:
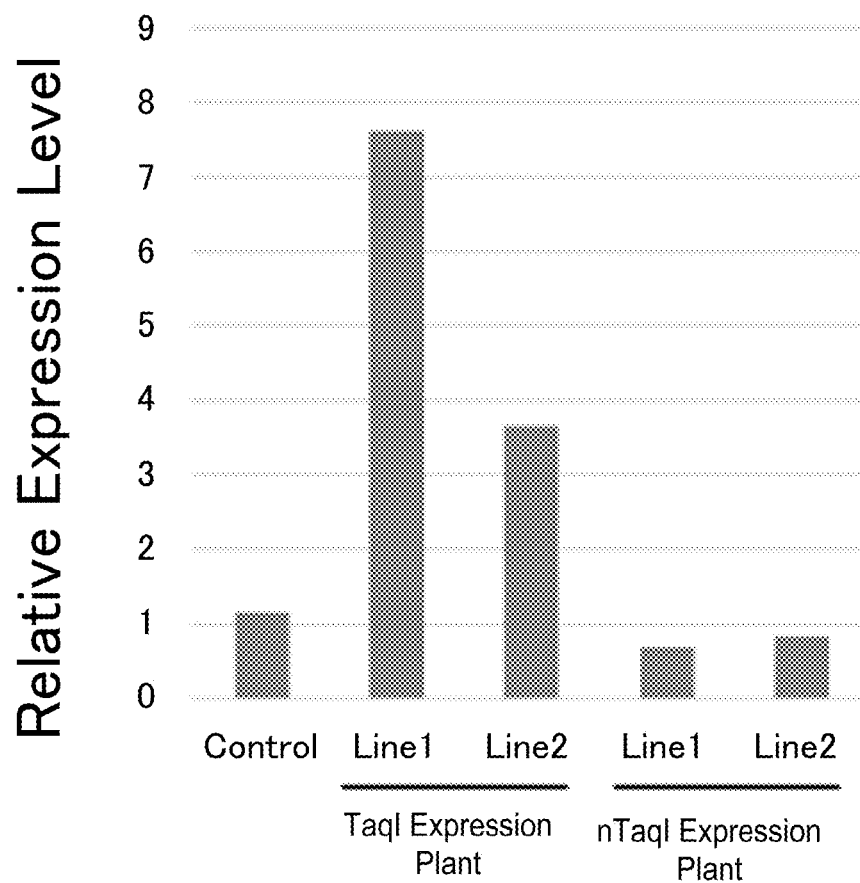
FIG. 1 shows relative expression levels of BRCA1 in protoplasts having introduced TaqI and nTaqI, respectively.

The present Description provides a fusion protein suitable for artificially regulating epigenomic states of genome DNA, and a use therefor. The fusion protein disclosed in this Description (hereunder also called "the fusion protein") may include a first region that defines a polypeptide capable of binding sequence-specifically to multiple sites on genome DNA, and a second region that defines a peptide capable of regulating an epigenomic state. The fusion protein is thus suited to directly regulating expression of multiple genes across a broad range.

Because such a fusion protein capable of regulating an epigenomic state can control epigenomic states at multiple sites on genome DNA, it can efficiently control gene expression rapidly and without genetic modification.

Moreover, because such a fusion protein is capable of efficient control (increase and decrease, etc.) of gene expression control in genome DNA, it can rapidly alter traits in a target organism. Furthermore, the fusion protein is also useful for genetic control in cases in which the target gene for a trait has not been identified, for efficiently modifying quantitative traits, for conferring new traits and the like, and for modification and functional analysis of epigenomic states.

In this Description, "genome DNA" may be genome DNA in a prokaryote or genome DNA in a cell nucleus of a eukaryote.

In this Description, an "epigenomic state" is a state in which histone or DNA or the like associated with gene expression is modified even though the DNA base sequence of the genome DNA is unchanged.

In this Description, the term "organism" includes prokaryotes and eukaryotes. Examples of prokaryotes include bacteria. Examples of eukaryotes include single-celled and multi-celled eukaryotic organisms. When a eukaryote is a multi-celled organism, the invention may be used with a part of the eukaryotic organism (such as a cell, tissue, organ or the like as described below).

Examples of eukaryotes include animals, plants, algae, bryophytes, and eukaryotic microorganisms. The animals are not particularly limited, but examples include mammals including non-human mammals, and various non-mammals such as fish and insects. These disclosures may also be applied to any form including tissues, organs, unfertilized eggs, sperm and fertilized eggs, as well as various cells including microbial cells, plants cells and animal cells such as cells from humans and non-human animals. In the case of an animal, a form such a fertilized egg that has the ability to regenerate a complete animal is convenient for obtaining a modified animal.

The plant used in the breeding method of the invention is not particularly limited, but examples include dicotyledonous and monocotyledonous plants. such as plants in the Brassicaceae, Gramineae, Solanaceae, Leguminosae and Salicaceae families and the like (see below).

Brassicaceae: *Arabidopsis thaliana, Brassica rapa, Brassica napus, Brassica oleracea* var. *capitata, Brassica rapa* var. *pekinensis, Brassica rapa* var. *chinensis, Brassica rapa* var. *rapa, Brassica rapa* var. *hakabura. Brassica rapa* var. *lanciniifolia, Brassica rapa* var. *perviridis, Raphanus sativus, Wasabia japonica*, etc.
Solanaceae: *Nicotiana tabacum, Solanum melongena, Solanum tuberosum, Lycopersicon lycopersicum, Capsicum annuum, Petunia*, etc.
Leguminosae: *Glycine max, Pisum sativum, Vicia faba, Wisteria floribunda, Arachis hypogaea, Lotus corniculatus* var. *japonicus, Phaseolus vulgaris, Vigna angularis, Acacia*, etc.
Asteraceae: *Chrysanthemum morifolium, Helianthus annuus*, etc.
Palmae: *Elaeis guineensis, Elaeis oleifera, Cocos nucifera, Phoenix dactylifera, Copernicia*, etc.
Anacardiaceae: *Rhus succedanea, Anacardium occidentale, Toxicodendron vernicifluum, Mangifera indica, Pistacia vera*, etc.
Cucurbitaceae: *Cucurbita maxima, Cucurbita moschata, Cucurbita pepo, Cucumis sativus, Trichosanthes cucumeroides, Lagenaria siceraria* var. *gourda*, etc.
Rosaceae: *Amygdalus communis, Rosa, Fragaria, Prunus, Malus pumila* var. *domestica*, etc.
Caryophyllaceae: *Dianthus caryophyllus*, etc.
Salicaceae: *Populus trichocarpa, Populus nigra, Populus tremula*, etc.
Gramineae: *Zea mays, Oryza sativa, Hordeum vulgare, Triticum aestivum, Phyllostachys, Saccharum officinarum. Pennisetum pupureum, Erianthus ravennae, Miscanthus virgatum, Sorghum, Panicum*, etc.
Liliaceae: *Tulipa, Lilium*, etc.
Myrtaceae: *Eucalyptus camaldulensis. Eucalyptus grandis*, etc.

The plant to which the fusion protein or the like is applied may be anything derived from a plant, but preferably has the ability to regenerate a complete plant. Thus, the plant may be in any form such as a protoplast or cell, various kinds of tissue, an organ or leaf, a plumule, axillary bud, lateral bud, adventitious bud, flower bud or other shoot, a shoot apex, stem or branch, a pistil or part thereof such as an ovule, a stamen or part thereof such as pollen, a seed or part thereof such as an embryo, a root or part thereof, or callus or the like.

The microorganisms are not particularly limited, but for purposes of material production and the like, examples include microbial cells including yeasts and molds such as koji molds and the like. Examples of koji molds include *Aspergillus* species such as *Aspergillus aculeatus* and *Aspergillus oryzae*. Various known yeasts may be used, and examples include *Saccharomyces* yeasts such as *Saccharomyces cerevisiae, Schizosaccharomyces* yeasts such as *Schizosaccharomyces pombe, Candida* yeasts such as *Candida shehatae, Pichia* yeasts such as *Pichia stipitis*, yeasts in the *Hansenula, Kloeckera, Schwanniomyces, Yarrowia, Trichosporon, Brettanomyces, Pachysolen* yeasts, *Yamadazyma* yeasts, *Kluyveromyces* yeasts such as *Kluyveromyces marxianus* and *Kluyveromyces lactis*, and *Issatchenkia* yeasts such as *Issatchenkia orientalis* and the like. Of these, a *Saccharomyces* yeast is desirable from the standpoint of industrial utility and the like, and *Saccharomyces cerevisiae* is especially desirable. A yeast may be either a heterothalistic yeast or a homothalistic yeast.

The algae are not particularly limited, and examples include eukaryotic single-celled organisms (diatoms, yellow-green algae, dinoflagellates, etc.) and multi-celled seaweeds (red algae, green algae, brown algae) and the like.

The bryophytes are not particularly limited, but examples include those that are non-vascular plants. Examples include mosses such as *Polytrichum juniperum* and *Hypnum plumaeforme* Wilson, liverworts such as *Marchantia polymorpha* L. and *Jungermannia*, and hornworts such as *Anthoceros* and the like.

Fusion Protein

The fusion protein may have a first region that defines a polypeptide capable of binding sequence-specifically at multiple sites on genome DNA and a second region that defines a polypeptide capable of regulating an epigenomic state. One or two or more of either the first region or the second region may be provided. Considering sequence-specificity for genome DNA and control of epigenomic states, one each of one kind each of the first region and second region may be provided.

First Region

The first region is a polypeptide (also called "the first polypeptide") that has DNA binding activity that recognizes a specific sequence on DNA, and can recognize the specific sequence and bind at multiple sites. The first polypeptide is a polypeptide having sequence specificity. The polypeptide used in this Description is a polypeptide that itself recognizes a specific sequence on DNA and demonstrates DNA binding activity. That is, the polypeptide itself or the polypeptide alone is a polypeptide capable of serving as a scaffold on genome DNA. With such a polypeptide, it is possible to ensure compact and accurate sequence-specific binding, and easily avoid off-target action.

For example, similar polypeptides include complexes using guide RNA (gRNA, sgRNA), such as complexes between guide RNA and Cas9 double mutants or Null mutants. However, the specific sequence binding of these complexes with DNA is based on DNA-RNA hybridization. Consequently, it is impossible to avoid off-target action which is non-specific binding to sequences other than the target sequence, and these complexes also cannot be purposely configured to allow them to bind to multiple sites. Moreover, because such complexes are originally designed to bind to a specific target site on genome DNA, they are different from the polypeptide intended by the present disclosure which can bind to multiple sites.

The first polypeptide may be a DNA binding protein such as zinc finger nuclease (ZFN) or transcription activator-like effector nuclease (TALEN), or a polypeptide derived from a restriction enzyme and lacking DNA double-strand cleavage activity. This is because these polypeptides have DNA-specific binding property that does not depend on polynucleotide hybridization, and do not cause DNA breaks because they lack DNA double-strand cleavage activity.

For example, a DNA recognition site of ZFN or TALEN may be modified to allow it to recognize a desired nucleotide sequence. In the case of a restriction enzyme, DNA double-strand cleavage activity can be deleted by substituting or deleting an amino acid residue that is essential for or contributes to the DNA double-strand cleavage activity.

ZFN or TALEN may be used as the first polypeptide, but in terms of intrinsic ability to act on multiple sites of genome DNA and binding accuracy based on sequence specificity, it is desirable to use a restriction enzyme having DNA binding activity but lacking DNA break activity.

This restriction enzyme is not particularly limited, and may be selected after appropriate consideration of the anticipated number of bindings (frequency) and anticipated binding sites and the like on genome DNA based on the recognition sequence of the restriction enzyme, as well as the optimum temperature and number of amino acid residues in the restriction enzyme and the like. If the nucleotide sequence of the genome DNA of the organism in which an epigenomic state is to be controlled is already known, a person skilled in the art can easily determine for example how many recognition sites for the recognition enzyme exist within a 1 kb range upstream from a gene. The recognition sequences of restriction enzymes have already been reported, and it is desirable to use TaqI, MunI, RAG1, EcoR124I, KpnI, Bsp6I and PvuII (see reference literature 1 to 8 below), for which DNA double-strand cleavage activity sites and DNA binding sites have already been reported.

The restriction enzyme recognition sequence is not particularly limited, but from the standpoint of control efficiency, for example DNA double-strand break enzymes called frequent restriction enzymes having roughly 4-bp to 6-bp recognition sites on the DNA double strand may be used. For example, a restriction enzyme having a 4-bp or 5-bp recognition site may be used. Also, a restriction enzyme having a 4-bp recognition site may be used.

In the case of a 4-bp recognition site for example, at least one, or for example two to seven, or for example three to six, or for example four to five, or for example five to seven recognition sites may be found within 1 kb upstream from a gene coding region that is a regulatory region of a gene. For example, in the case of TaqI, which has a 4-bp recognition site, with respect to the genome DNA of *Arabidopsis thaliana*, the number of genes having one recognition site within 1 kb upstream from the gene is at least 5,000, the number of genes having two recognition sites is nearly 6,000, the number of genes having three recognition sites is at least 5,000, the number of genes having four recognition sites is about 3,500, the number of genes having five recognition sites is at least 2,000, and the number of genes having six recognition sites is at least 1,000. Thus, diversity can be introduced into many genes using a modified restriction enzyme having a 4-bp to 5-bp recognition site.

From the standpoint of improving sequence specificity, the recognition sequence of the restriction enzyme preferably recognizes a palindromic sequence in genome DNA. Recognition accuracy is improved when a palindromic sequence is recognized.

From the standpoint of the recognition site, examples include, but are not limited to, ApeKI, BsrI, BssKI, BstNI, BstUI, BtsCI, FatI, FauI, HinPII, PhoI, PspGI, SmlI, TaqI, TfiI, TseI, Tsp45I and TspRI. Various known frequent restriction enzymes such as Sse9I, MseI, DpnI and CviAII may also be used.

The optimal temperature for a restriction enzyme applied to the first polypeptide is also not particularly limited. For example, a restriction enzyme derived from a thermophile may be used. A thermophile is a bacteria with an optimal growth temperature of at least 45° C. or a growth limit temperature of at least 55° C. Thermophiles are generally archaea. Furthermore, a restriction enzyme derived from a thermophile may generally have a deactivation temperature of 80° C. or greater. A restriction enzyme derived from a thermophile has an optimal temperature of about 50° C. to 80° C.

With a restriction enzyme derived from a thermophile, the optimal temperature for DNA double-strand cleavage activity, or in other words the temperature at which DNA double-strand break enzyme activity is generally the highest (also called the incubation temperature), is at a temperature range higher than the normal growth temperatures of organisms. Using a first polypeptide derived from such a restriction enzyme, it tends to be easier to ensure sequence-specific binding of the first polypeptide. Furthermore, using a first polypeptide derived from such a restriction enzyme, it may be possible to activate, enhance or reduce the sequence-specific binding activity of the fusion protein by temperature treatment with the desired timing and intensity. Such a restriction enzyme also allows sequence-specific binding activity to be regulated by means of temperature. Furthermore, relatively gentle sequence-specific binding activity can also be achieved by using such a restriction enzyme at a temperature lower than the optimal temperature.

Such a restriction enzyme may have an optimal temperature of 50° C., 55° C., 60° C., 65° C. or 75° C. (all catalog values) for example. The optimal temperature of a restriction enzyme can be selected based on catalogs (catalog values) provided by various vendors. If the optimal temperature is below 50° C., sequence-specific binding may be too strong. If the optimal temperature exceeds 80° C., sequence-specific binding may be too weak. For example, the optimal temperature may be at least 55° C., or at least 60° C. for example, or at least 62° C., or about 65° C. The optimal temperature may also be not more than 75° C., or not more than 70° C. for example, or not more than 68° C. for example.

For example, a restriction enzyme from which the first polypeptide is derived may be selected and used appropriately from the following known restriction enzymes.

TABLE 1

| Optimal Temperature ° C. | Restriction Enzyme |
|---|---|
| 50 | ApoI |
| | BclI |
| | BfuAI |
| | BspQI |
| | BssHII |
| | BtsCI |
| | Nt.BspQI |
| | SfiI |
| 55 | BsiWI |
| | BslI |
| | BsmAI |
| | BsmBI |
| | BtsI |
| | FatI |
| | FauI |
| | Nt.BstNBI |
| | SmlI |
| | Sse9I |
| 60 | BsaBI |
| | BsaJI |
| | BsaWI |
| | BsiEI |
| | BssKI |
| | BstAPI |
| | BstEII |
| | BstNI |
| | BstUI |
| | BstYI |
| | BtgZI |
| | MwoI |
| | AccIII(BspM) |
| 65 | BsiHKAI |
| | BsmFI |
| | BsmI |
| | BsrDI |
| | BsrI |
| | BstBI |
| | Nb.BsmI |
| | Nb.BsrDI |
| | PI-PspI |
| | TaqI |
| | TfiI |
| | TseI |
| | Tsp45I |
| | Tsp509I |
| | TspRI |
| | Tth111I |
| 75 | ApeKI |
| | PhoI |
| | PspGI |
| | TspMI |

Of those above, examples include ApeKI, BsaBI, BsaJI, BsaWI, BsiEI, BslI, BsmBI, BsmI, BspQI, BsrDI, BsrI, BssKI, BstAPI, BstBI, BstNI, BstUI, BstYI, FatI, FauI, MwoI, Nb.BsmI, Nb.BsrDI, PspGI, SfiI, SmlI, TaqI, TfiI, TliI, TseI, Tsp45I, Tsp509I, TspMI, TspRI, Tth111I and the like from the standpoint of optimal temperature.

A restriction enzyme having an optimal temperature for DNA double-strand cleavage activity of less than 50° C. may also be used as the restriction enzyme from which the first polypeptide is derived. A restriction enzyme having an optimal temperature of less than 45° C. may also be used.

An enzyme having an optimal temperature for DNA double-strand cleavage activity in the normal temperature range (normal temperature restriction enzyme) may also be used as the restriction enzyme from which the first polypeptide is derived. "Normal temperature range" here means for example 15° C. to 42° C., or for example 15° C. to 40° C., or for example 25° C. to 40° C., or for example 25° C. to 37° C., or for example 30° C. to 37° C.

A normal temperature restriction enzyme has an optimal temperature of about 25° C. to 40° C. (typically 25° C. or 37° C.). Furthermore, a normal temperature restriction enzyme can be deactivated by incubation at roughly 60° C. to 80° C. for 15 to 20 minutes. The temperature at which the restriction enzyme is deactivated when incubated for 15 to 20 minutes is called the deactivation temperature. In some cases, a normal temperature restriction enzyme may also have a deactivation temperature of 80° C. or more.

By adjusting the amount (expressed amount) of the restriction enzyme, the timing, temperature and duration of the enzyme action and other conditions as necessary, the normal temperature restriction enzyme can be made to break DNA efficiently in cells while avoiding the adverse effects of these conditions (especially temperature and the like) on organisms.

Adjustment of conditions such as action temperature and duration can also be simplified in some cases because the normal temperature restriction enzyme has a certain degree of sequence-specific binding activity at the temperatures normally applied to organisms (growth temperatures).

A commercially available restriction enzyme with an optimal temperature of 25° C. to 40° C. (typically 25° C. or 37° C.) may be used as the normal temperature restriction enzyme. For example, a commercial restriction enzyme having such an optimal temperature and also having a deactivation temperature of 60° C. to 80° C. may be used.

A known restriction enzyme derived from a non-thermophilic bacteria may also be selected and used appropriately as a restriction enzyme derived from a non-thermophilic bacteria.

Example of such restriction enzymes include, but are not limited to, AluI, HhaI, HinPII, MseI, MboI, HaeIII and the like. These all have optimal temperatures of 37° C. Other examples include BfaI, Bful, Bsh1236I, BsuRI, DpnI, DpnII, FspBI, HinII, Hin6I, HpaII, HpyCH4IV, MspI, NlaIII, RsaI, Sau3AI and the like. The restriction enzymes listed above all have optimal temperatures of about 37° C. Other examples include ApaI, BaeI, BspCNI, CviAII, CviQI, SmaI and SwaI, which all have optimal temperatures of about 25° C.

Optimal temperatures for the activity of proteins such as restriction enzymes having DNA double-strand cleavage activity are described in the protocols of the providers of those enzymes, and can also be based on the results of an evaluation of enzyme reactions performed at various temperatures with a specific concentration of a specific substrate in a buffer that is considered suitable for that enzyme.

For example, methods for measuring the optimal temperatures of restriction enzymes are described in the literature (Greene, P. J., Poonian, M. S., Nussbaum, A. L., Tobias, L., Garfin, D. E., Boyer, H. W. & Goodman, H. M. (1975), Restriction and modification of a self-complementary octanucleotide containing the Eco RI substrate, Journal of Molecular Biology, 99(2), 237-261). Specifically, breaking of ($^{32}$P labeled) SV40 DNA by the restriction enzyme is analyzed quantitatively. That is, 5 μl of a restriction enzyme solution (0.05 M potassium phosphate buffer (pH 7.0), 0.02 M NaCl, 0.02% NP40, 0.1 mM EDTA, 0.7 mM β-mercaptoethanol, 0.7 pM restriction enzyme) is added to a total of 50 µl of a reaction solution (0.1 M Tris HCl (pH 7.5), 5 mM $MgCl_2$, 0.05 mM $MgCl_2$, 0.05 M NaCl, 1.6 pM SV40 DNA), and restriction enzyme treatment is performed for a suitable time of roughly a few minutes at different temperatures (temperatures set at appropriately temperature intervals between 0° C. and 80° C.). 1% SDS is added to stop the reaction, and supercoil DNA (form I), open circle DNA (form II) and linear DNA (form III) are then isolated by agarose gel electrophoresis. The dose (cpm) of each form is measured, and the number of excised phosphodiester bonds (pmol) due to restriction enzyme treatment is calculated by the following formula. The numbers of excised phosphodiester bonds at each temperature are graphed, and a temperature around the peak value is given as the optimal temperature (for DNA double-strand cleavage activity) of the enzyme.

Phosphodiester bonds (pmol)=[2×(dose of form III (cpm)+dose of form II (cpm))/(total dose of forms I, II and III (cpm))]×amount of DNA (pmol)

The deactivation temperatures of proteins such as restriction enzymes having DNA double-strand cleavage activity can also be obtained for example by measuring activity before and after heat treatment in which the enzyme is maintained for about 15 to 20 minutes at each temperature. The temperature at which no activity is detected is the deactivation temperature.

When a restriction enzyme is used as the first polypeptide, it is desirable to modify an amino acid residue that is necessary for the DNA double-strand cleavage activity of the restriction enzyme but has no effect or only a restricted effect on the DNA binding activity. For example, an amino acid residue can be modified by introducing a mutation such as substitution, deletion or insertion of an amino acid. The form of modification and the number of modifications are not particularly limited, but preferably sequence-specific binding activity is not too greatly reduced, and other conditions necessary for DNA binding are not too greatly affected.

The DNA double-strand cleavage activity sites and DNA binding sites of many restriction enzymes have been analyzed. For example, those for TaqI, MunI, RAG1, EcoR124I, KpnI, Bsp6I, PvuII and the like are reported in Reference Literature 1 to 8 below. The entire contents described in this reference literature are incorporated by reference in this Description.

Reference Literature 1 (for TaqI): The Journal of Biological Chemistry, Vol. 273, No. 49, p. 33002 (1998)

Reference Literature 2 (for MunI): Biochemistry, 1997, 36(37), 11086

Reference Literature 3 (for SfiI): Nucleic Acids Res. 2009 September; 37(16): 5443-53, doi: 10.1093/nar/gkp569, Epub 2009 Jul. 13

Reference Literature 4 (for RAG1): J. Mol. Biol. 2009 Jul. 31; 390(5): 863-78, doi: 10.1016/j.jmb.2009.05.076, Epub 2009 Jun. 3

Reference Literature 5 (for EcoR124I): J. Mol. Biol. 2008 Feb. 15; 376(2): 438-52, doi: 10.1016/j.jmb.2007.11.024, Epub 2007 Nov. 17

Reference Literature 6 (for KpnI): Nucleic Acids Res. 2007; 35(8): 2777-86, Epub 2007 Apr. 11

Reference Literature 7 (for Bsp6I, PvuII): Nucleic Acids Res. 2005 Jan. 31; 33(2): 661-71, Print 2005

Reference Literature 8 (general): Nucleic Acids Res. 2001 Sep. 15; 29(18): 3705-27, Review In the case of TaqI for example, it has been reported that the D137 site is essential for DNA double-strand cleavage activity but has little or only a restricted effect on DNA binding activity, while for example amino acid residue substitution mutations to D137A, D137V and D137G can delete DNA double-strand cleavage activity while retaining sequence-specific binding activity while (Reference Literature 1).

Even when such a report is not available for a restriction enzyme, a person skilled in the art can suppress or delete DNA double-strand cleavage activity while maintaining sequence-specific binding activity by introducing site-specific mutations or comparing the conformations of similar restriction enzymes. Techniques for modifying polypeptides by introduction of site-specific mutations are well known to those skilled in the art.

Second Region

The second region of the fusion protein can define a polypeptide capable of regulating an epigenomic state. The state of an organism or individual is characterized not only by genes and gene expression control based on the nucleotide sequences of genome DNA, but also by states that do not depend on the nucleotide sequence of genome DNA, namely the chemical modification states of genome DNA and the chemical modification states (epigenomic states) of the histones making up chromosomes. The second region defines a polypeptide (hereunder called the second polypeptide) that chemically modifies DNA or chemically modifies histones.

The second polypeptide is a polypeptide having DNA methylation activity for example. DNA methylation may be for example a methylation addition reaction to the 5-position carbon atom on the pyrimidine ring of cytosine or the 6-position nitrogen atom on the purine ring of adenine. In mammals, DNA methylation of cytosine normally occurs at the CpG site, but in plants it is thought to occur at the CpHpG site and CpHpH site as well as the CpG site of cytosine.

A polypeptide having DNA methylation activity may be a DNA methyltransferase for example. In mammals, examples of DNA methyltransferases include DNMT1, DNMT3a, DNMT3b, DNMT3L and DNMT2.

In plants, examples include DRM2 (de novo-type DNA methyltransferase), MET1 (CpG sequence-retaining DNA methyltransferase) and CMT3 (non CpG sequence-retaining DNA methyl transferase). The DRM2 and MET1 proteins have high homology with the methyltransferases DNMT3 and DNMT1 of mammals, respectively, but the CMT3 protein is a protein only found in plants.

The second polypeptide is also a polypeptide having DNA demethylation activity. Examples of this polypeptide include TET1 (DNA demethylase) in mammals, and ROS1 (DNA demethylase) and DME (DNA demethylase) in plants and the like.

The second polypeptide is also a polypeptide having histone chemical modification activity. The histone chemical modification activity is not particularly limited, but may be any selected from the group consisting of histone acetylation, histone deacetylation, histone methylation, histone demethylation, histone ubiquitination, histone deubiquitination, histone phosphorylation, histone dephosphorylation and the like. Of these, examples include histone acetylation, histone deacetylation, histone methylation, histone demethylation and histone ubiquitination.

Examples of histone acetyltransferases (HATs) include p300 (human to nematode) and CBP (human to nematode) in the CBP/p300 (CREB binding protein) family, Gcn5

(human to yeast), PCAF (human, mouse), Hat1 (human to yeast), Elp3 (human to yeast) and ATF-2 (human to yeast) in the GNAT family, Esa1 (yeast), MOF (*Drosophila*), Sas2 (yeast), Sas3 (yeast), MORF (human), Tip60 (human) and Hbo1 (human) in the MYST family, and SRC1 (human, mouse) and ACTR (human, mouse) in the SRC family and the like.

In terms of polypeptides having histone deacetylation activity, there are five families of histone deacetylation enzymes (HDACs), called Class I (HDAC1, 2, 3, 8), Class IIa (HDAC4, 5, 7, 9), Class IIb (HDAC6, 10), Class III (SIRT1 to 7) and Class IV (HDAC11).

Examples of polypeptides having histone methylation activity include histone methylation enzymes (HMTs) such as Suv39H1 (human, mouse), Suv39H2 (human, mouse), G9a (human), Set9 (human), EZH2 (human), DOTIL (human), SETDB (human), KYP (*Arabidopsis*), DIMS (*Neurospora*), Clr4 (*Schizosaccharomyces*), Set1 (*Saccharomyces*) and the like.

Examples of polypeptides having histone demethylation activity include LSD1 (human), KDM6A/UTX (human), KDM6B/JMJD3 (human), KDM2/7JMJC subfamily (human), JMJC domain-containing histone demethylase (human) and the like.

Examples of polypeptides having histone ubiquitination activity include Rad6 (yeast), USP/UBP (*Arabidopsis*), UBP26, OTLD1 and the like.

The amino acid sequences of such polypeptides capable of regulating epigenomic states, and the nucleotide sequence encoding those amino acid sequences, can be obtained by a person skilled in the art by appropriately searching NCBI and the like.

The mode in which the first and second regions are provided as part of the fusion protein is not particularly limited. For example, the first region may be provided at the N-end, the C-end or another part of the fusion protein. The second region may also be provided at the N-end, the C-end or another part of the fusion protein.

The fusion protein may also include another polypeptide as appropriate. For example, it may include a nuclear translocation signal (such as -Pro-Pro-Lys-Lys-Lys-Arg-Lys-Val-) (SEQ ID NO: 18).

For research purposes, the fusion protein may also be provided for example with a labeling polypeptide or a polypeptide capable of binding to a known labeling substance. When such a label or the like is provided, it is possible to observe the condition or the like of the fusion protein as it binds sequence-specifically to genome DNA, or to separate genome DNA using the label.

For purposes of separation and collection, the fusion protein may also be provided as necessary with a His tag or other polypeptide or antibody for affinity binding, or a part or antigen thereof.

The fusion protein may be obtained as an artificial protein including the first region and second region. For example, the fusion protein can be obtained by chemical or genetic engineering based on the amino acid sequences of the first polypeptide and second polypeptide. A person skilled in the art can obtain the fusion protein by appropriate methods once they have obtained the amino acid sequences and nucleotide sequences of the first polypeptide and second polypeptide. Linking of the first polypeptide and second polypeptide can be accomplished by appropriately using a known peptide linker.

Because the fusion protein has a first polypeptide that binds sequence-specifically at multiple sites on genome DNA, epigenomic states can be changed all at once at multiple sites on genome DNA with one kind of first polypeptide.

When using a restriction enzyme as the first polypeptide, an epigenomic state can be altered with high reproducibility based on the high sequence-specific binding accuracy of the restriction enzyme. Also, gene expression control can be changed (increased, reduced, etc.) broadly and/or rapidly using a restriction enzyme because it is capable of altering epigenomic states at a very large number of genome DNA sites.

When using a restriction enzyme, moreover, restriction enzymes with multiple recognition sequences are already known. Diverse epigenomic states can therefore be changed in diverse ways using the sequence-specific binding property and accuracy of such restriction enzymes.

Polynucleotide

The polynucleotide disclosed in this Description is a polynucleotide (hereunder also called "the polynucleotide") encoding the fusion protein. The polynucleotide is itself useful as an epigenomic state control agent. The polynucleotide may be either single-stranded DNA or double-stranded DNA, or single-stranded RNA, or a DNA-RNA hybrid or DNA-RNA chimera or the like. This means that it may be any capable of encoding the amino acid sequence of the polypeptide as data. The polynucleotide may be in the form of single-stranded or double-stranded DNA or single-stranded or double-stranded RNA for example.

The polynucleotide may be in the form of a construct such as an expression vector including a coding region encoding the amino acid sequence of the fusion protein together with a control region for expressing the fusion protein as a protein (polypeptide).

Vector

The present Description provides an expression vector (hereunder also called "the expression vector") including the polynucleotide. The expression vector is designed to cause expression of information (the amino acid sequence of the fusion protein) encoded by the polynucleotide. The expression vector may include the polynucleotide together with one or two or more control regions for causing expression of a polypeptide encoded by the polynucleotide. Examples of control regions include promoters as well as terminators, selection markers, enhancers, and nucleotide sequences for improving translation efficiency and the like.

The promoter is not particularly limited as long as it is a promoter capable of causing expression of the fusion protein in a target eukaryotic cell, and a known promoter may be used favorably. In plants, examples of such promoters include cauliflower mosaic virus 35S promoter (CaMV35S), various actin gene promoters, various ubiquitin gene promoters, nopaline synthase gene promoter, tobacco PR1a gene promoter, tomato ribulose 1,5-bisphosphate carboxylase oxidase small subunit gene promoter, napin gene promoter and the like.

As discussed below, a promoter such as the *Arabidopsis thaliana* sigma factor-derived SIG2 (AtSIG2) promoter having expression intensity lower than that of the 35S promoter may be desirable as a low-expression constitutive promoter for causing constant expression of the polypeptide at a low level. Furthermore, an inducible promoter as discussed below such as the *Arabidopsis thaliana* HSP18.2 promoter or the like may be able to induce expression of a gene under control at a temperature lower than the induction temperature, and may be useful as a low-expression constitutive promoter for expressing the fusion protein.

An inducible promoter may also be used as a promoter. An inducible promoter may can cause the fusion protein to act inducibly via specific expression induction in eukaryotes. It is thus possible to express the action of the fusion protein with the desired timing. Examples of such inducible promoters include inducible promoters that are induced by chemical substances or concentrations of chemical substances such as galactose or copper ions, or by external conditions such as light, heat and osmotic pressure. These various inducible promoters are selected appropriately according to the type of target eukaryote. For example, known inducible promoters including copper ion-responsive promoters and other metallothionein promoters, galactose-inducible promoters, tetracycline-inducible promoters, DEX-inducible promoters, heat shock protein promoters such as HSP18.2 promoters, and induction systems using known transcription factors and the like may be selected appropriately.

Site-specific promoters and time-specific promoters may also be used. By site-specifically or time-specifically inducing expression of the polypeptide, it is possible to express the fusion protein and exert its activity with the desired timing and at the desired site. It is also possible to stop induction or generally reduce or stop the action of the polypeptide after a specific period of time. Examples of such site-specific promoters and time-specific promoters include promoters that cause expression of specific genes in specific tissues at specific times in plants and in specific tissues at specific times in animals. In plants for example, these include seed-specific promoters, flower-specific promoters, and sieve tissue-specific promoters. In animals, they include reproductive cell-specific promoters, and various promoters specific to times, organs and the like.

Regulating the expression intensity of the fusion protein with control elements such as promoters and terminators may also affect the binding activity and control activity of the fusion protein. Consequently, the expression intensity of the fusion protein under the control of the promoter or terminator also needs to be considered when selecting a promoter or the like.

The terminator is not particularly limited as long as it functions as a transcription termination site, and a known one may be used. For example, a nopaline synthase gene transcription termination region (Nos terminator), cauliflower mosaic virus 35S transcription termination region (CaMV35S terminator) or the like may be used by preference. Of these, a Nos terminator is especially desirable.

In addition, known elements may be selected and used appropriately as selection markers and nucleotide sequences for increase translation efficiency. The method for constructing the expression vector is not particularly limited, and the necessary elements may be introduced appropriately into an appropriately selected host vector as necessary. The expression vector may also have a T-DNA region.

In plant cells for example, various conventional known vectors for plants may be used as the host vector for the expression vector for expressing the protein. Examples of virus vectors include plant virus vectors such as tobacco mosaic virus (TMV), plum pox virus (PPV), potato virus X (PVX), alfalfa mosaic virus (AIMV), cucumber mosaic virus (CMV), cowpea mosaic virus (CPMV) and zucchini yellow mosaic virus (ZYMV). Apart from these plant virus vector, a pBI binary vector may be used by preference when the vector introduction method is a method using *Agrobacterium*. Specific examples of pBI binary vectors include pBIG, pBIN19, pBI101, pBI121 and pBI221. A known transient gene expression vector may also be used.

A vector designed for expressing the fusion protein in a plant, an animal such as a mammal or fish or a eukaryotic microorganism such as a yeast can be constructed by a person skilled in the art by conventional known methods according to the type of target organism and the appropriate transformation techniques. A vector suited to the organism for introduction may be obtained appropriately, suitable promoters, terminators, enhancers and the like may also be selected appropriately, and a desired expression cassette may also be constructed as necessary.

When preparing the expression vector, a person skilled in the art can apply standard DNA recombination techniques (see for example Molecular Cloning. Third Edition, 1.84. Cold Spring Harbor Laboratory Press, New York) such as methods using restriction enzymes and DNA ligases to the various recombination operations according to the type of target organism and the intended conditions for expressing the fusion protein and the like.

The polynucleotide and expression vector encode the fusion protein, so like the fusion protein, they are useful as epigenomic state control agents for genome DNA. The fusion protein and expression vector can be introduced into an organism such as a eukaryote by a known gene introduction method such as an electroporation method, virus infection method, particle gun method. *Agrobacterium* infection method, peptide method, calcium chloride method, microinjection method, liposome method, polyethylene glycol method, cell fusion method or the like according to the type of organism or cell, and the fusion protein can then be synthesized to obtain the functions of the polypeptide included in the fusion protein.

Cell

The present Description also provides a cell (hereunder sometimes called "the cell") containing the polynucleotide or the vector. Because epigenomic states of genome DNA can be controlled with this cell, gene expression can be controlled efficiently and traits can be rapidly altered in the cell. Although this is not a limitation, the cell is preferably configured with the polynucleotide or vector carried within a chromosome or outside a chromosome, in such a way that expression of the fusion protein is retained after cell division.

Examples of cells are not particularly limited, but include cells of the organisms described above. The type of cell is also not particularly limited, but examples include stomatic cells, reproductive cells, fertilized eggs, embryonic stem cells, iPS cells and the like. The cell may be a cell of a eukaryote or the like as explained above, or an individual eukaryote or part of a eukaryote. In the case of an animal for example, these include individual animals as well as organs, tissues and the like. In the case of a plant, they include individual plants as well as callus, seedlings, leaves, flower buds, shoot apices, lateral buds, flower buds, pollen, ovaries, endosperm and embryos, seeds and other reproductive materials and the like.

Because the epigenomic states of genome DNA can be controlled with the cell, it is possible to obtain desired traits such as useful traits and the like. Such cells or tissues containing the cells (including individual organisms) can be screened based on useful traits to obtain a eukaryote with efficiently modified traits or the like.

A person skilled in the art who can obtain the fusion protein, the polypeptide and the vector can also obtain the cell using transformation techniques well known to those skilled in the art according to the type of cell.

Kit

The present Description also provides a kit provided with either the fusion protein, the polynucleotide, the vector or the cell. With this kit it is possible to efficiently regulate gene expression, and rapidly alter the traits of a cell or the like.

Method for Controlling Epigenomic State

The present Description provides a method of regulating an epigenomic state (hereunder also called "the regulation method"), including the steps of: preparing the fusion protein so that it can act on genome DNA, and using the fusion protein to alter an epigenomic state. With this regulation method, it is possible to directly and efficiently regulate an epigenomic state of genome DNA using the fusion protein as a scaffold for genome DNA and as a genome DNA modification element.

Preparation Step

In the preparation step, the fusion protein is prepared so that it can act on genome DNA. For the fusion protein, the various embodiments of the first region, second region and fusion protein explained above may be applied. Preparing the fusion protein so that it can act on genome DNA means for example that the vector containing the polynucleotide encoding the fusion protein is prepared by a method suited to the organism in which the epigenomic state is to be controlled. Typically, a vector may be prepared according to the type of organism and the like. The various embodiments explained above may be adopted for the polynucleotide and the vector.

Step of Altering Epigenomic State

In the epigenomic state altering step, by taking advantage of the sequence-specific binding property of the first region of the fusion protein, the fusion protein is delivered to a sequence-specifically recognized site on genome DNA, where the second region is allowed to act on the genome DNA to alter an epigenomic state. When the fusion protein is expressed in a cell, it binds to genome DNA based on sequence specificity, and alters an epigenomic state of genome DNA at or near that site.

The culture temperature of the cell or the growth temperature of the organism may be set as necessary so as to obtain the sequence-specific binding property of the first region of the fusion protein, although this is not a limitation. This is because when the first region is derived from a restriction enzyme, its sequence-specific binding property is affected by the optimal temperature for DNA double-strand cleavage activity determined by the restriction enzyme.

In a cell or organism with an altered epigenomic state obtained by this regulation method, the degree of alteration can be evaluated appropriately by known epigenomic state analysis methods, or by the phenotype observation disclosed in the examples or the like.

The regulation method may also be implemented as a method for producing a eukaryote or the like in which an epigenomic state is under artificial control. In this case, an individual plant can be reproduced or an animal can be obtained from a cell, eukaryote or part of a eukaryote obtained by the alteration step. Conventional known methods may be used for these methods.

In this regulation method, DNA methylation/demethylation, histone acetylation/deacetylation, hi stone methylation/demethylation, histone ubiquitination/deubiquitination or the like occurs due to the action of the second region of the fusion protein. These chemical modifications regulate gene expression and the like without breaking or modifying genome DNA. Because these changes allow rapid expression control such as control (increase or decrease) at the gene transcription level, they can be immediately confirmed as phenotypic changes. It is also easy to change a trait (phenotype) of an organism because binding can be accomplished at multiple sites on genome DNA based on the sequence-specificity of the fusion protein.

With the regulation method, it is also possible to simultaneously modify and change epigenomic states at multiple sites based on the sequence-specificity of the fusion protein. This means that the action of just one kind of fusion protein can change organism's traits all at once or cause major changes. To modify multiple sites simultaneously, it is advantageous to modify quantitative traits of an organism.

When a polypeptide derived from a restriction enzyme is used as the first polypeptide of the fusion protein, moreover, highly reliable gene expression control is possible because highly precise sequence-specific binding to genome DNA can be expressed due to the high specificity of the recognition sequence.

By using the sequence-specific binding property of multiple existing restriction enzymes, moreover, it is possible to modify and change multiple epigenomic states on genome DNA, and control expression of diverse genes.

This regulation method can change the traits of an organism by controlling epigenomic states with a high degree of sequence specificity at multiple sites on the genome DNA of the organism. The resulting organism or a part thereof can then be used to analyze epigenomic states by known methods, or in other words the DNA and histone modification states can be analyzed to search for genes associated with the resulting trait.

Other

As the first polypeptide of the fusion protein, a polypeptide having the sequence-specific binding property of a restriction enzyme but lacking DNA double-strand cleavage activity can sequence-specifically label genome DNA when used as a fusion protein linked to another labeling polypeptide or a polypeptide that binds to a labeling substance. Accurate labeling at multiple sites on genome DNA can be accomplished with high accuracy by using the highly precise sequence specificity of the restriction enzyme.

This fusion protein can be obtained by fusing a known labeling polypeptide or label-binding polypeptide by known methods.

EXAMPLES

Concrete examples of the disclosures of this Description are explained below. However, the examples below are intended to explain the disclosures and not to limit their scope.

Example 1

Preparation of Plant nTaqI (TaqI Lacking DNA Double-Strand Cleavage Activity) Expression Vector Using a TaqI sequence linked to a pGEM-T vector (Promega KK) as a template (see Japanese Patent Application Publication No. 2011-160798), with a complementary primary set (SEQ ID NOS: 1 and 2) for introducing a target nucleotide substitution (D137A nucleotide substitution inactivating DNA double-strand cleavage activity of TaqI) disclosed in the literature (Cao, W. and Barany, F. (1998) Identification of TaqI endonuclease active site residues by $Fe^{2+}$-mediated oxidative cleavage, J. Biol. Chem. 273, 33002-33010), a PCR reaction was performed with Prime-Star (Takara Bio Inc.) to amplify the full vector sequence.

```
                                          (SEQ ID NO: 1)
nTaqI-1_F: gccacctgggagttggCcgcccaggggatagat (SEQ ID NO: 2)
nTaqI-1_R: atctatccctgggcgGccaactcccaggtggc
```

The residual template vector in the resulting PCR product was digested overnight at 37° C. by DpnI (NEB) treatment, and the product was purified by ethanol sedimentation. The purified DNA sample was transformed into ECOS Competent *E. coli* DH5a (Nippon Gene Co., Ltd.), coated on LB+100 µg/ml Carbecinillin-containing solid medium, and grown overnight at 37° C. to obtain a transformant. Several of these transformed *E. coli* colonies were picked up and liquid cultured, after which a plasmid was extracted with a plasmid extractor.

A sequence reaction (BigDye Terminator v3.1 Cycle Sequencing Kit, Applied Biosystems) was performed with M13R and M13F primers (SEQ ID NOS: 3 and 4) from the resulting plasmid, and the product was purified by ethanol sedimentation, after which the sequences were analyzed with a 3130 Genetic Analyzer (Applied Biosystems) to confirm that the nucleotide substitution had been introduced at the target position.

```
                                (SEQ ID NO: 3)
M13F: cgccagggttttcccagtcacgac (SEQ ID NO: 4)
M13R: tcacacaggaaacagctatgac
```

The nTaqI sequence was then introduced into a pBI121 vector (provided with a cauliflower mosaic virus 35S promoter) so that it could be expressed in plant cells.

Example 2

Analysis of Genome Breaking and Homologous Recombination Due to nTaqI Introduction in Protoplast An *Arabidopsis thaliana* transformant was prepared using the vector prepared in Example 1. The *Agrobacterium* method was used. The wetting method of Clough et al. (Steven J. Clough and Andrew F. Bent, 1998, The Plant Journal 16, 735-743) used in Japanese Patent Application Publication No. 2011-160798 was used as the *Agrobacterium* method up to the T1 seed stage.

Confirming Relative Expressed Amount of BRCA1 in Transformant

To confirm the DNA double-strand break (DSB) effect of the restriction enzyme, the *Arabidopsis thaliana* T1 seeds obtained above were sprouted, and about one week later the plants were heat treated for 24 hours at 37° C., RNA was extracted, and gene expression of BRCA1, which is an important factor for DNA break repair, was analyzed (see Kim, S. A., Punshon, T., Lanzirotti, A., Li, L. Alonso, J. M., Ecker, J. R. Kaplan, J. and Guerinot, M. L. (2006), Localization of iron in *Arabidopsis* seed requires the vacuolar membrane transporter VIT1, Science, 314 (5803), 1295-1298). RNA was extracted with an RNeasy Plant Mini Kit (Qiagen) in accordance with the manufacturer's protocols. cDNA was synthesized from the extracted RNA with a reverse transcription kit, after which real-time PCR analysis was performed with a Power SYBR Green PCR master mix (Life Technologies). The reverse transcription reaction and real-time PCR analysis were also performed in accordance with the manufacturer's instruction. 18rRNA (detection primers; SEQ ID NOS: 5 and 6) was measured as an internal standard, and the expressed amount of the DSB repair gene BRCA1 (detection primers; SEQ ID NOS: 7 and 8) was also analyzed as a relative expressed amount. The results are shown in FIG. 1.

```
                                    (SEQ ID NO: 5)
18SrRNA-F:      CGGCTACCACATCCAAGGAA (SEQ ID NO: 6)
18SrRNA-R:      TGTCACTACCTCCCCGTGTCA (SEQ ID NO: 7)
BRCA1-F:        CCATGTATTTTGCAATGCGTG (SEQ ID NO: 8)
BRAC1-R:        TGTGGAGCACCTCGAATCTCT
```

FIG. 1 shows relative values for expressed amount of BRCA1 (expressed amount of BRCA1 in sample/expressed amount of 18SrRNA in sample). Neither heat treatment (24 hours at 37° C.) nor nTaqI overexpression caused any great change in BRCA1 expression in comparison with the vector control. However, the expressed amount of BRCA1 did rise significantly in the TaqI expression strain, which was identical except that it carried TaqI instead of nTaqI. This suggests that the DNA repair system was not activated in response to DSB in the nTaqI expressing plant.

Confirming DNA Recombination Frequency in nTaqI-Introduced Strain of *Arabidopsis Thaliana*

Next, the T1 *Arabidopsis thaliana* seeds obtained above were sterilized, vernalized, and sown in MS agar medium containing 1% sucrose. After sowing these were grown for two weeks under 22° C. long-day conditions, and GUS staining was performed with the entire plant body. Heat treatment was performed for three hours or 24 hours at 37° C. for one week after germination. GUS staining was performed by the known methods of Kim et al. 90% acetone was first poured into a 1.5 ml microtube, and cooled in advance to 4° C. The plant body was soaked in the 90% acetone, and left standing on ice until sampling was completed. After completion of all sampling, it was left standing for 20 minutes at room temperature. The tube was rotated two or three times during this process to gently agitate the acetone solution and sample. This was then rinsed three times in 50 mM phosphate buffer (pH 7.0), after which X-Glue solution (1.9 mM X-Gluc (5-bromo-4-chloro-3-indolyl-b-D-glucuronide-cyclohexylammonium salt), 0.5 mM $K_3Fe(CN)_6$, 0.5 mM $K_4[Fe(CN)_6].3H_2O$, 0.3% Triton X-100, 50 mM phosphate buffer, pH 7.0) was substituted.

The sample was then depressurized at a pressure of 0.075 MPa (10 seconds, twice) to cause the X-Gluc solution to permeate the sample, and left standing overnight at 37° C. The stained tissue appeared blue. Once staining was confirmed, 70% EtOH was substituted to stop the staining reaction and decolorize the chlorophyll and the like. After thorough decolorization, the stained plant body was observed. The results are shown in FIG. 2.

Figure 2:
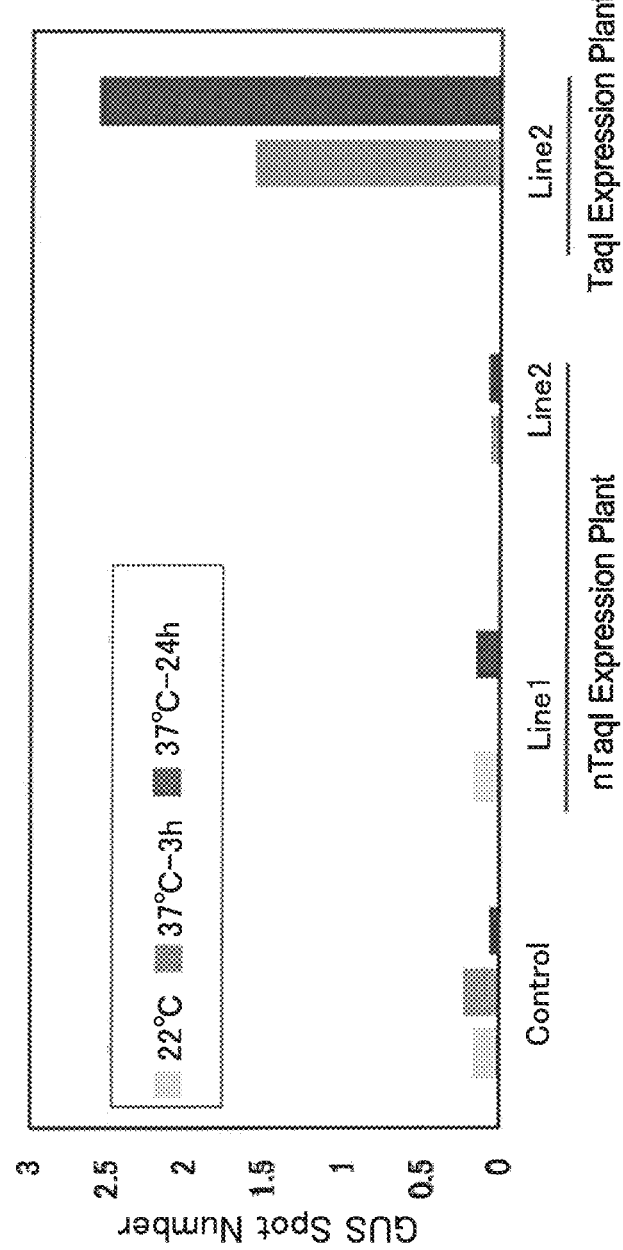
FIG. 2 shows numbers of GUS spots indicating DNA recombination sites which TaqI and nTaqI were introduced, respectively.

As shown in FIG. 2, nTaqI overexpression and heat treatment (3 hours or 24 hours at 37° C.) caused no great change in the number of GUS spots in comparison with the vector control. On the other hand, there was a large difference in GUS spots in the TaqI expressing strain. This suggests that the DNA recombination accompanying DSB was not activated in the nTaqI expressing plant.

Example 3

Figure 3:
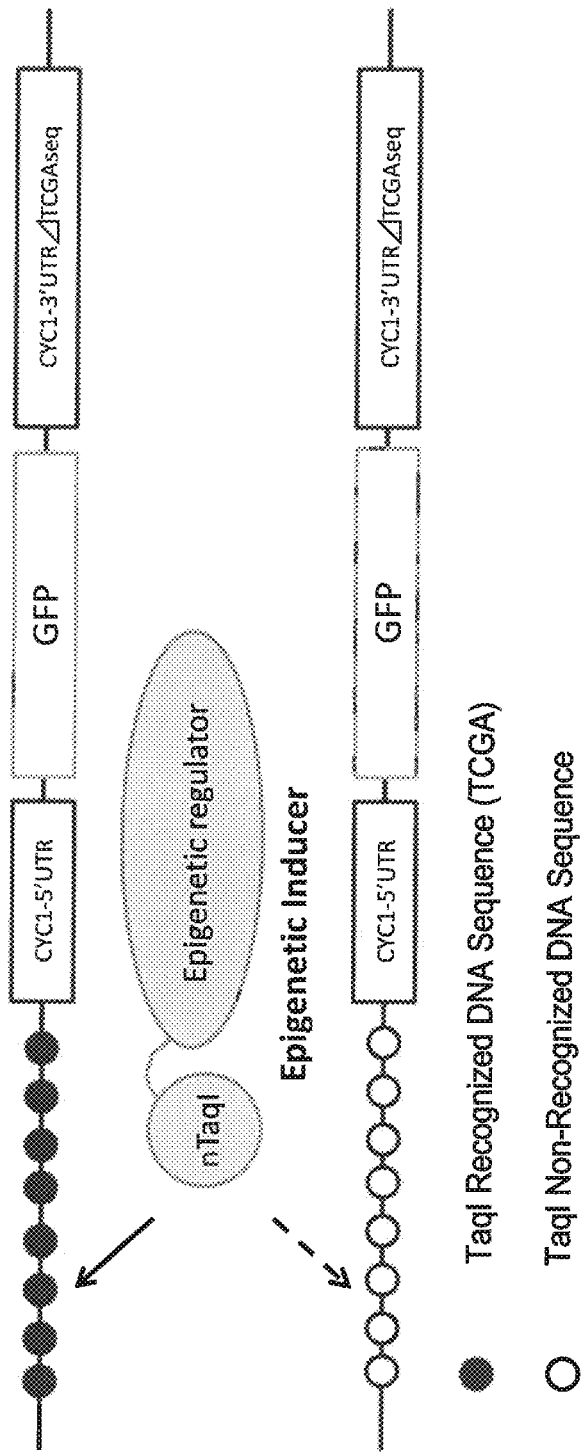
FIG. 3 illustrates an outline of a construct for evaluating changes in epigenomic states caused by fusion proteins in yeasts.

Verifying Principle of Epigenomic State Change Using Fusion Protein of nTaqI with Epigenomic State Control Factor To investigate whether a fusion protein (epigenetic inducer: EI) of nTaqI with an epigenomic state control factor (epigenetic regulator: ER) could induce gene expression changes through epigenomic state changes in a living organism, a GFP reporter assay was performed in a budding yeast. An outline is shown in FIG. 3. Specifically, a reporter gene was prepared having an artificial promoter based on an artificial sequence including eight TaqI recognition sequences (TCGA) and 240 bp upstream from the CYC1 gene (TCGA×8) (SEQ ID NO: 9), and an artificial terminator having two TCGA sequences deleted by substituting A for T in the TCGA sequences each 270 bp downstream from a GFP gene and the CYC1 gene (SEQ ID NO: 10). A reporter gene using an artificial promoter having no TaqI recognition sequence (TCGA×0) (SEQ ID NO: 11) was also prepared for purposes of comparison. The prepared reporter genes were inserted into the BY4742 budding yeast strain to prepare yeasts for evaluation (BY4742+GFP).

```
Artificial Promoter (TCGA x 8)
                                          (SEQ ID NO: 9)
CGACATCGTCGAATATGATTACTCACCAATCGATTTACCGGTTCCTTTGT

CGATATCATGTTGGGACGCTCGAAGGCTTTATTTAGTTGTCGACTGATAC

TTGACTTCATCGAGACTTTCAGACCACGATCGATGGTCACTAATCCTCGA

GCAGATCCGCCAGGCGTGTATATATAGCGTGGATGGCCAGGCAACTTTAG

TGCTGACACATACAGGCATATATATATGTGTGCGACGACACATGATCATA

TGGCATGCATGTGCTCTGTATGTATATAAAACTCTTGTTTTCTTCTTTTC

TCTAAATATTCTTTCCTTATACATTAGGACCTTTGCAGCATAAATTACTA

TACTTCTATAGACACACAAACACAAATACACACACTAAAT

Artificial Terminator
                                          (SEQ ID NO: 10)
ACAGGCCCCTTTTCCTTTGACGATATCATGTAATTAGTTATGTCACGCTT

ACATTCACGCCCTCCTCCCACATCCGCTCTAACCGAAAAGGAAGGAGTTA

GACAACCTGAAGTCTAGGTCCCTATTTATTTTTTTTAATAGTTATGTTAG

TATTAAGAACGTTATTTATATTTCAAATTTTTCTTTTTTTTCTGTACAAA

CGCGTGTACGCATGTAACATTATACTGAAAACCTTGCTTGAGAAGGTTTT

GGGACGCACGAAGGCTTTAA

Artificial Promoter (TCGA x 0)
                                          (SEQ ID NO: 11)
GCAGATCCGCCAGGCGTGTATATATAGCGTGGATGGCCAGGCAACTTTAG

TGCTGACACATACAGGCATATATATATGTGTGCGACGACACATGATCATA

TGGCATGCATGTGCTCTGTATGTATATAAAACTCTTGTTTTCTTCTTTTC

TCTAAATATTCTTTCCTTATACATTAGGACCTTTGCAGCATAAATTACTA

TACTTCTATAGACACACAAACACAAATACACACACTAAAT
```

HAT histone acetylation enzymes (SWC4, RTT109) and CR chromatin remodeling composite factors (CHD1, TTI1) from budding yeasts were used as the ERs for fusing with nTaqI.

Yeast expression induction vectors were prepared including the 3'UTR terminator of the *Saccharomyces cerevisiae* DIT1 protein together with EIs obtained by fusing each ER to nTaqI downstream from a galactose inducible promoter. These vectors were transformed into the evaluation yeast (BY4742+GFP) with a Frozen-EZ Yeast Transformation II Kit (Zymo Research), to obtain transformants. Each transformant was cultured overnight at 30° C. with YPD medium (10 g/L yeast extract, 20 g/L peptone, 20 g/L glucose) containing 1.0 mg/L Aureobasidin A (AbA), the medium was replaced with YPG (10 g/L yeast extract, 20 g/L peptone, 20 g/L galactose) containing 1.0 mg/L AbA, and induction culture was performed for 18 hours at 25° C. to perform EI expression induction.

The culture solutions before and after induction were stained with propidium iodide (PI), and the PI and GFP fluorescence intensity of $1 \times 10^5$ yeast cells were measured with a SH800 flow cytometer manufactured by Sony Corporation. The average value of GFP fluorescence intensity in a population (live cells) without PI fluorescence was calculated, and GFP fluorescence intensity with or without the TCGA sequence was compared before and after expression induction. The results are shown in FIG. 4.

Figure 4:
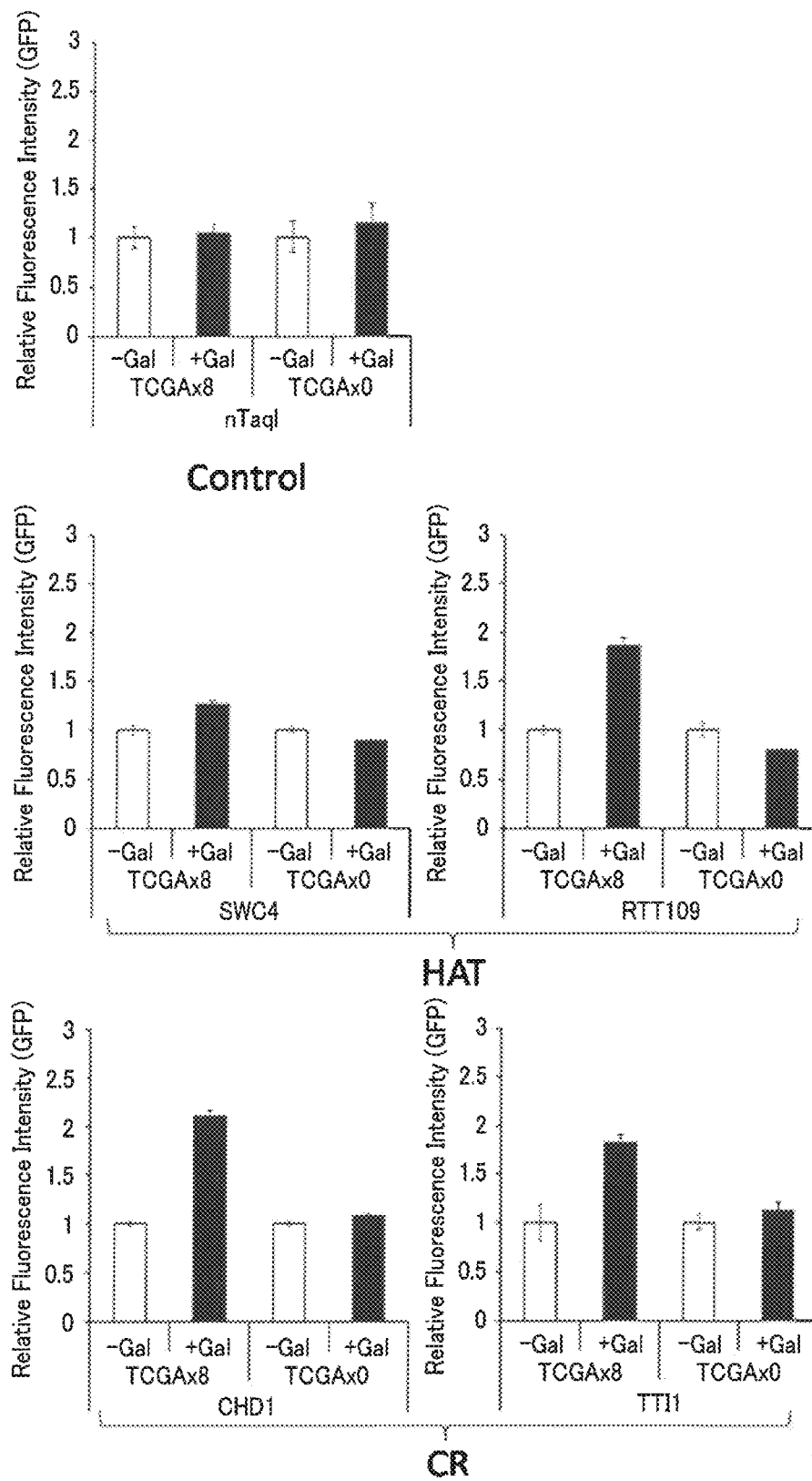
FIG. 4 shows evaluation results for changes in epigenomic states in yeasts according to the epigenomic state control factor.

As shown in FIG. 4, no change in GFP fluorescence intensity was seen when only nTaqI expression was induced, but with HAT (SWC4, RTT109) and CR (CHD1, TTI1), GFP fluorescence intensity rose only when there was expression induction (+Gal) and TCGA sequences were present (TCGA×8). From these results, it appears that the genomic structure relaxed and GFP expression increased due to FIAT and CR recruited by nTaqI near the TaqI recognition sequence, showing that epigenomic state changes can be induced by an EI.

Example 4

Confirming Effects on Growth of Introduction into Plants

As shown in Table 2, plasmids were prepared including epigenomic state modification factors linked at the 3' end of the nTaqI sequence in a plant nTaqI expression vector, and introduced into *Arabidopsis thaliana* by the methods performed in Example 2. The modification factors shown in Table 2 are enzymes that generally perform DNA methylation and demethylation, histone acetylation and deacetylation and histone methylation and demethylation. It should be possible to select these from a wide range of eukaryotes such as humans, *Arabidopsis*, and yeasts. These expression vectors were introduced into *Arabidopsis thaliana*, plants were obtained, and changes in the leaves were observed.

TABLE 2

| DNA-bind | modification | CR-factor | Origin | Phenotype |
| --- | --- | --- | --- | --- |
| nTaqI | none | none | none | Normal |
| nTaqI | His-Ac | p300-CD | Human | Stress tolerance |
| nTaqI | DNA-DeMet | TET1-CD | NP_085128 | Growth |
| nTaqI | His-DeMet | LSD1 | NP_055828.2 | Growth |
| nTaqI | Recr_His-mod | KRAB | Human | |
| nTaqI | Recr_His-mod | Sin3a | AT1G24190 | |
| nTaqI | His-DeAc | HDA6 | AT5G63110 | Growth, Flower |
| nTaqI | His-DeAc | HDA19 | AT4G38130 | |
| nTaqI | His-Met | KYP | AT5G13960 | |
| nTaqI | His-Met | SUVH5 | AT2G35160 | |
| nTaqI | His-Ac | GCN5 | AT3G54610 | |
| nTaqI | DNA-Met | MET1-CD | AT5G49160 | Growth |
| nTaqI | DNA-DeMet | ROS1 | AT2G36490 | |
| nTaqI | DNA-Met | DRM2 | AT5G14620 | |
| nTaqI | DNA-Met | CMT3 | AT1G69770 | |

When artificial genes including nTaqI fused to the DNA demethylation enzyme TET1, the histone demethylation enzyme LSD1, the histone deacetylation enzyme HDA6 and the DNA methylation enzyme MET1 were expressed in plants, morphological leaf changes (growth), late flowering and the like were observed. This suggests that by itself, expression of fused proteins including nTaqI and various epigenomic regulators in plants contributes to gene expression and quantitative trait changes.

Example 5

Effects of Fusion Protein Introduction on Salt Stress Resistance in Plants

Next, responsiveness to salt stress was analyzed using plants constantly expressing nTaqI-p300 (human-derived histone acetylation enzyme). Good growth was observed under ordinary growth conditions (MS medium). This is similar to what occurs when either nTaqI or p300 is constantly expressed by itself. Thus, this confirms that expression of these individually does not greatly affect plant growth.

A transformed seedling that had been grown for one week after sowing under ordinary growth conditions (MS medium) was transplanted into MS medium containing 200 mM of sodium chloride, and subsequent growth was observed to analyzed stress responsiveness. The results are shown in FIG. 5 and FIG. 6.

Figure 5:
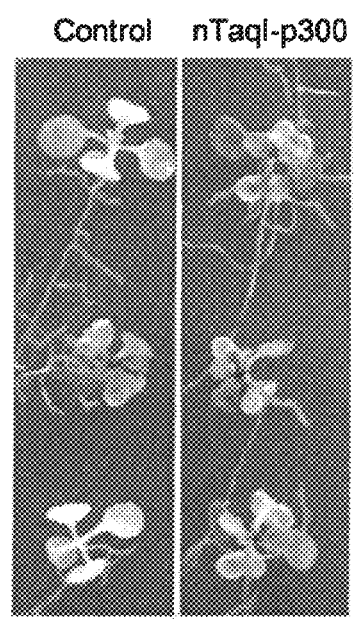
FIG. 5 shows the effects of nTaqI-p300 introduction on salt stress in *Arabidopsis thaliana*.
Figure 6:
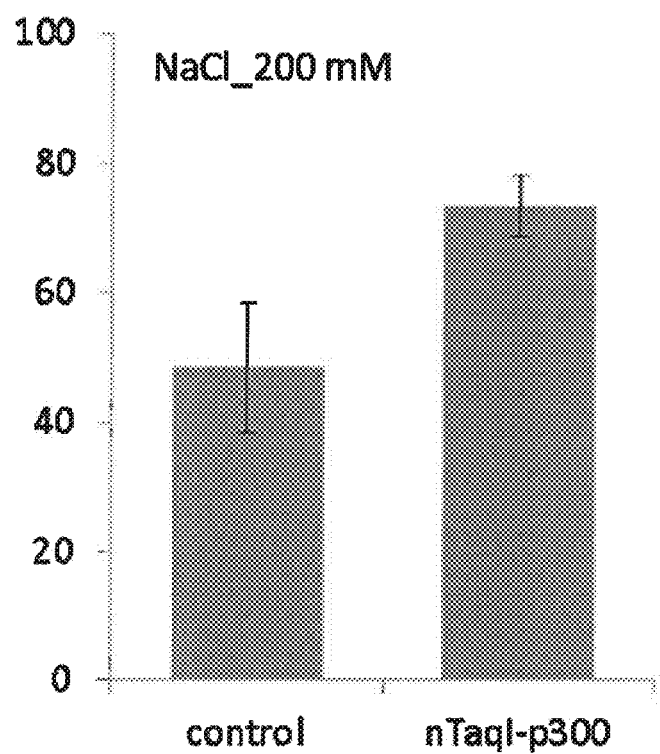
FIG. 6 shows the effects of nTaqI-p300 introduction on salt stress in *Arabidopsis thaliana*.

As shown in FIG. 5 and FIG. 6, the plant constantly expressing nTaqI-p300 exhibited good growth in comparison with the control. This suggests that nTaqI-p300 expression helps to confer stress resistance.

Example 6

Effects of Fusion Protein Introduction on Heat Stress Resistance in Plants

Responsiveness to heat stress was evaluated using the same plant strain used in Example 5. This was grown for two weeks after sowing in MS medium, subjected to temporary heat treatment for one hour at 45° C., and then grown for one week under 22° C. growth conditions. The results are shown in FIG. 7.

Figure 7:
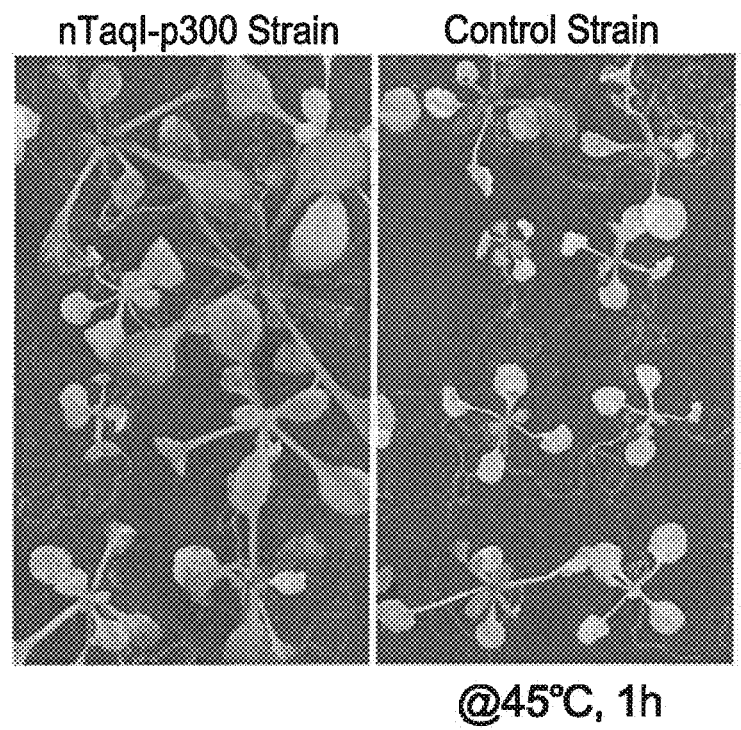
FIG. 7 shows the effects of nTaqI-p300 introduction on heat stress in *Arabidopsis thaliana*.

As shown in FIG. 7, the plant constantly expressing nTaqI-p300 exhibited good growth in comparison with the control. This suggests that nTaqI-p300 expression helps to confer heat stress resistance as well as salt stress resistance.

Example 7

Effects of Fusion Protein Introduction on Expression of Heat Stress Responsiveness Genes in Plants To confirm the expression behavior of heat responsiveness genes under heat stress conditions, RNA was extracted from plants during heat treatment, and expression of the typical heat responsiveness gene factors At3g09640, At5g05410 and At5g12020 (Proceedings of the National Academy of Sciences, 103(49), 18822-18827) was analyzed. RNA was extracted with an RNeasy Plant Mini Kit (Qiagen) in accordance with the manufacturer's protocols. cDNA was first synthesized from the extracted RNA with a reverse transcription kit, and real-time PCR analysis was performed with a Power SYBR Green PCR master mix (Life Technologies). The reverse transcription reaction and real-time PCR analysis were also performed in accordance with the manufacturer's instruction. 18rRNA (detection primers; SEQ ID NOS: 3 and 4) was measured as an internal standard, and expressed amounts of heat responsiveness genes (detection primers; SEQ ID NOS: 12 to 17) were also analyzed. The expressed amount of the BRCA1 gene was also assayed as a relative value (BRCA1 expression in sample/18SrRNA expression in sample), and the difference between the values with and without heat treatment was shown as a relative value. The results are shown in FIG. 8.

```
                                           (SEQ ID NO: 12)
    At3g09640 -F: tttcatcctggtagactggaca (SEQ ID NO: 13)
    At3g09640 -R: cacatctcttagatgatccacacc (SEQ ID NO: 14)
    At5g05410 -F: gattttcaaatttcgtcccc (SEQ ID NO: 15)
    At5g05410 -R: ctccactctgatcataaactgc (SEQ ID NO: 16)
    At5g12020 -F: acccttcacgagtttacatgc (SEQ ID NO: 17)
    At5g12020 -R: gcgttagggtgctcgatg
```

Figure 8:
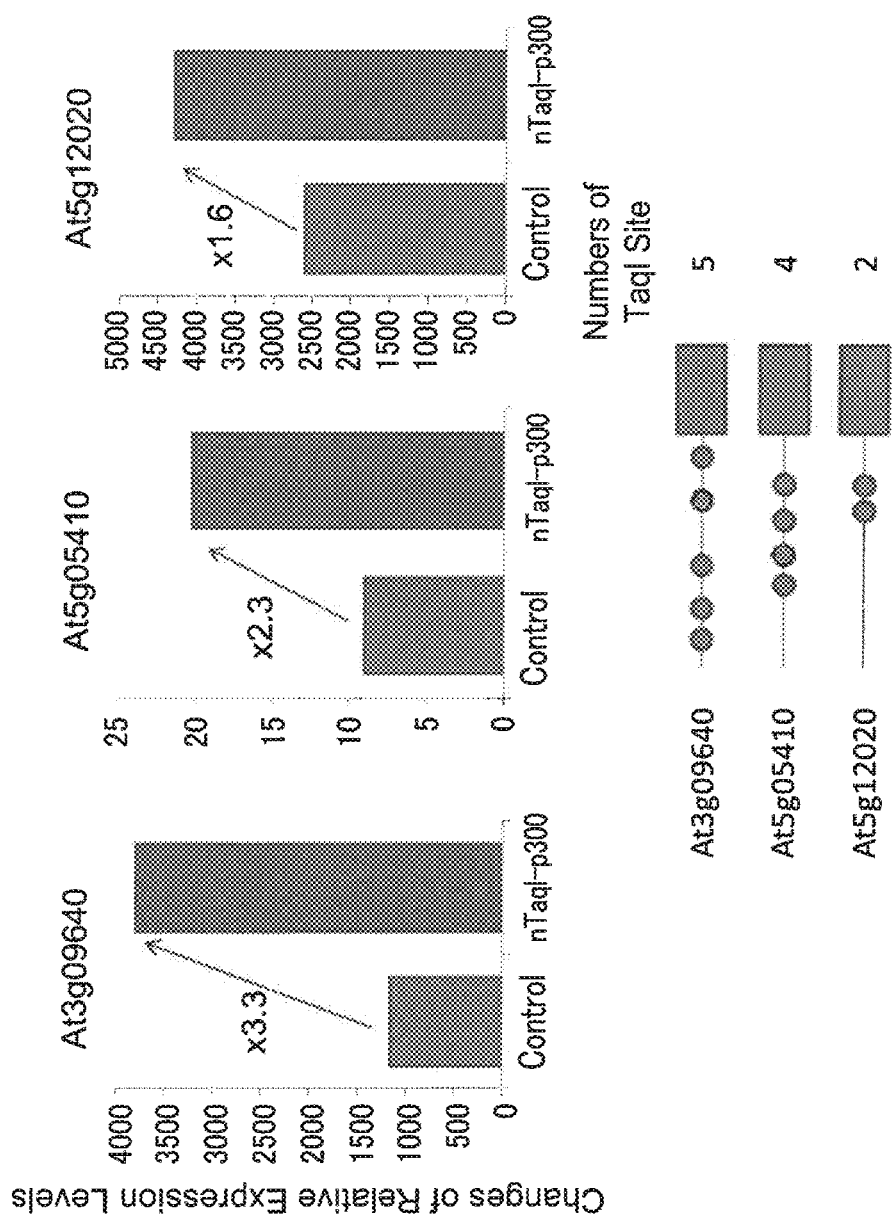
FIG. 8 shows the effects of nTaqI-p300 introduction on expression of thermoresponsive genes in *Arabidopsis thaliana*.

As shown in FIG. 8, nTaqI-p300 overexpression and heat treatment caused a significant rise in heat responsiveness gene expression in comparison with the vector control. The degree of increase in comparison with the control was also dependent on the number of TaqI sites in the promoter region (500 bp) of each gene. This suggests that in plants expressing nTaqI-p300, gene expression is broadly regulated via the TaqI sites.

The patent documents and articles described in this Description are incorporated by reference in this Description.

---

The invention claimed is:

1. A fusion protein comprising:
a first region comprising a polypeptide capable of binding sequence-specifically to multiple sites on genome DNA; and
a second region comprising a polypeptide capable of regulating an epigenomic state of the genome DNA, wherein the polypeptide of the first region is derived from a restriction enzyme having a base sequence of 4 bases or more and 6 bases or less as a recognition site and lacking DNA double-strand break activity.

2. The fusion protein according to claim 1, wherein the restriction enzyme is a frequent restriction enzyme.

3. The fusion protein according to claim 1, wherein the polypeptide of the first region is derived from a 4-base recognition restriction enzyme.

4. The fusion protein according to claim 1, wherein the polypeptide of the first region has an activity of recognizing and binding to a palindromic sequence in genome DNA.

5. The fusion protein according to claim 1, wherein the polypeptide of the first region is derived from a frequent restriction enzyme, and has an activity of recognizing and binding to a palindromic sequence in genome DNA.

6. The fusion protein according to claim 1, wherein the polypeptide of the second region has DNA methylation activity, DNA demethylation activity and/or histone chemical modification activity.

7. The fusion protein according to claim 6, wherein the histone chemical modification activity is selected from the group consisting of histone acetylation, histone deacetylation, histone methylation, histone demethylation, histone ubiquitination and histone deubiquitination.

8. A method comprising:
expressing the fusion protein according to claim 1 so that the fusion protein is capable of acting on the genome DNA in a cell; and
altering epigenomic states of the genome DNA in the cell by modifying the specific sites of the genome DNA without DNA double-strand cleavage on the sites by taking advantage of the sequence-specific binding property of the first region and the genome DNA regulating property of the second region.

9. The method according to claim 8, wherein the epigenomic states at the multiple sites on the genomic DNA are altered simultaneously.

10. The method according to claim 8, wherein the fusion protein is allowed to act inductively.

11. The method according to claim 8, wherein a trait of an organism is altered.

12. The method according to claim 8, wherein a quantitative trait of an organism is altered.

13. The method according to claim 8, wherein the organism is a plant.

14. The method according to claim 8, wherein the organism is a yeast.

15. The method according to claim 8, wherein the genome DNA is genome DNA within an animal cell derived from a human.

16. The method according to claim 8, which is a method of breeding a non-human organism.

17. A polynucleotide encoding the fusion protein according to claim 1.

18. A vector containing the polynucleotide according to claim 17.

19. A cell containing the polynucleotide according to claim 17 and expressing the fusion protein.

20. A kit including the fusion protein according to claim 1, a polynucleotide encoding the fusion protein, a vector containing the polynucleotide or a cell containing the polynucleotide.

21. The fusion protein according to claim 1, wherein:
the polypeptide of the first region is derived from a frequent restriction enzyme and has an activity of recognizing and binding to a palindromic sequence and/or a 4-base recognition sequence in genome DNA; and
the polypeptide of the second region has DNA methylation activity, DNA demethylation activity and/or histone chemical modification activity selected from the group consisting of histone acetylation, histone deacetylation, histone methylation, histone demethylation, histone ubiquitination and histone deubiquitination.

22. The fusion protein according to claim 1, wherein the polypeptide of the first region is derived from TaqI modified to lack DNA double-strand cleavage activity.

* * * * *